United States Patent [19]

Takahashi et al.

[11] Patent Number: 4,727,083
[45] Date of Patent: Feb. 23, 1988

[54] FUNGICIDAL COMPOSITION EMPLOYING NITROBENZENE DERIVATIVES

[75] Inventors: Junya Takahashi, Hyogo; Hiroshi Noguchi; Yukio Oguri, both of Toyonaka; Shigeo Yamamoto; Toshiro Kato, both of Takarazuka; Katsuzo Kamoshita, Osaka, all of Japan

[73] Assignee: Sumitomo Chemical Company, Limited, Osaka, Japan

[21] Appl. No.: 911,867

[22] Filed: Sep. 26, 1986

[30] Foreign Application Priority Data

Sep. 27, 1985 [JP] Japan .................. 60-216045

[51] Int. Cl.$^4$ ............. A01N 33/18; A01N 37/18; A01N 43/52; A01N 43/76
[52] U.S. Cl. ................... 514/376; 514/365; 514/391; 514/395; 514/421; 514/479; 514/617; 514/716
[58] Field of Search ........... 514/716, 365, 376, 391, 514/395, 421, 479, 617

[56] References Cited

FOREIGN PATENT DOCUMENTS 2056362 3/1971 Fed. Rep. of Germany ...... 514/716

Primary Examiner—Allen J. Robinson
Attorney, Agent, or Firm—Birch, Stewart, Kolasch & Birch

[57] ABSTRACT

A fungicidal composition which comprises as an active ingredient a compound of the formula:

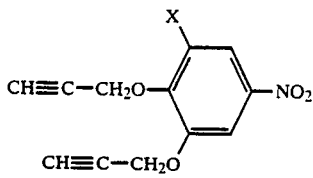

wherein X is a halogen atom, a $C_1$–$C_3$ alkyl group or a $C_1$–$C_3$ alkoxy group, and an inert carrier or diluent.

17 Claims, No Drawings

FUNGICIDAL COMPOSITION EMPLOYING NITROBENZENE DERIVATIVES

The present invention relates to a fungicidal composition, and more particularly, it relates to a fungicidal composition comprising a certain nitrobenzene derivative.

Benzimidazole and thiophanate fungicides such as Benomyl (methyl 1-(butylcarbamoyl)benzimidazol-2-ylcarbamate), Fuberidazol (2-(2-furyl)benzimidazole), Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)-benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene are known to exhibit an excellent fungicidal activity against various plant pathogenic fungi, and they have been widely used as agricultural fungicides since 1970. However, their continuous application over a long period of time permits phytopathogenic fungi to develop a tolerance to them, whereby their plant disease-preventive effect is significantly lowered. Further, the fungi which developed tolerances to certain kinds of benzimidazole or thiophanate fungicides also demonstrate considerable tolerance to show some other kinds of benzimidazole or thiophanate fungicides. Thus, they are apt to develop cross-tolerances. Therefore, if any material decrease in their plant disease-preventive effect in certain fields is observed, their application to such fields has to be discontinued. However, it is often observed that the density of drug-resistant organisms is not decreased even long after the discontinuation of the application. Although other kinds of fungicides have to be employed in such a case, only few are so effective as benzimidazole or thiophanate fungicides in controlling various phytopathogenic fungi.

Cyclic imide fungicides such as Procymidone (3-(3',5'-dichlorophenyl)-1,2-dimethylcyclopropane-1,2-dicarboximide), Iprodione (3-(3',5'-dichlorophenyl)-1-isopropylcarbamoylimidazolidine-2,4-dione), Vinchlozolin (3-(3',5'-(dichlorophenyl)-5-methyl-5-vinyloxazolidin-2,4-dione), ethyl (RS)-3-(3',5'-dichlorophenyl)-5-methyl-2,4-dioxooxazolidine-5-carboxylate, etc., which are effective against various plant diseases, particularly those caused by Botrytis cinerea, have the same defects as previously explained with respect to the benzimidazole or thiophanate fungicides.

As a result of a study seeking a new type of fungicide, it has now been found that nitrobenzene derivatives of the formula:

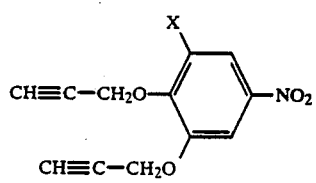

wherein X is a halogen atom, a $C_1$-$C_3$ alkyl group or a $C_1$-$C_3$ alkoxy group, show an excellent fundicidal activity against plant pathogenic fungi which have developed resistance to benzimidazole, thiophanate and/or cyclic imide fungicides. It is notable that their fungicidal potency against the organisms tolerant to benzimidazole, thiophanate and/or cyclic imide fungicides (hereinafter referred to as "drug-resistant fungi" or "drug-resistant strains") is much higher than that against the organisms sensitive to benzimidazole, thiophanate and/or cyclic imide fungicides (hereinafter referred to as "drug-sensitive fungi" or "drug-sensitive strains").

The dipropargyloxy-nitrobenzene compounds (I) are fungicidally effective against a wide scope of plant pathogenic fungi, of which specific examples are as follows: Podosphaera leucotricha, Venturia inaequalis, Mycosphaerella pomi, Marssonina mali and Sclerotinia mali of apple, Phyllactinia kakicola and Gloeosporium kaki of persimmon, Cladosporium carpophilum and Phomopsis sp. of peach, Cercospora viticola, Uncinula necator, Elsinoe ampelina and Glomerella cingulata of grape, Cercospora beticola of sugarbeet, Cercospora arachidicola and Cercospora personata of peanut, Erysiphe graminis f. sp. hordei, Cercosporella herpotrichoides and Fusarium nivale of barley, Erysiphe qraminis f. sp. tritici of wheat, Sphaerotheca fuliginea and Cladosporium cucumerinum of cucumber, Cladosporium fulvum of tomato, Corynespora melongenae of eggplant, Sphaerotheca humuli, Fusarium oxysporum f. sp. fragariae of strawberry, Botrytis alli of onion, Cercospora apii of cerely, Phaeoisariopsis griseola of kidney bean, Erysiphe cichoracearum of tobacco, Diplocarpon rosae of rose, Elsinoe fawcetti, Penicillium italicum, Penicillium digitatum of orange, Botrytis cinerea of cucumber, eggplant, tomato, strawberry, pimiento, onion, lettuce, grape, orange, cyclamen, rose or hop, Sclerotinia sclerotiorum of cucumber, eggplant, pimiento, lettuce, celery, kidney bean, soybean, azuki bean, potato or sunflower, Sclerotinia cinerea of peach or cherry, Mycosphaerella melonis of cucumber or melon, etc. Namely, the dipropargyloxy-nitrobenzene compounds (I) are highly effective in controlling the drug-resistant strains of the fungi.

The dipropargyloxy-nitrobenzene compounds (I) are also fungicidally effective against fungi sensitive to known fungicides as well as fungi to which known fungicides are ineffective. Examples of such fungi are Pyricularia oryzae, Pseudoperonospora cubensis, Plasmopara viticola, Phytophthora infestans, etc.

Advantageously, the dipropargyloxy-nitrobenzene compounds (I) are low in toxicity and have little detrimental effects on mammals, fish and so on. Also, they may be applied to agricultural fields without causing any material toxicity to important crop plants.

Among the dipropargyloxy-nitrobenzene compounds (I), 3-chloro-4,5-dipropargyloxy-nitrobenzene is known [Japanese Patent Publn. (unexamined) No. 83148/1986], but its fungicidal activity has never been reported.

The dipropargyloxy-nitrobenzene compound (I) can be prepared by reacting the corresponding dihydroxynitrobenzene compound of the formula:

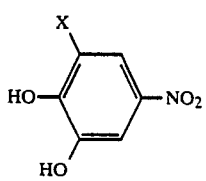

wherein X is as defined above with a propargyl halide of the formula:

CH≡C—CH₂—Y wherein Y is a halogen atom.

The reaction is usually carried out in an inert solvent (e.g. water, benzene, toluene, xylene, diethyl ether, tetrahydrofuran, dioxane, chloroform, carbon tetrachloride, ethyl acetate, pyridine, N,N-dimethylformamide), or a mixture of two or more inert solvents. The reaction may be performed in the presence of a base (e.g. pyridine, triethylamine, N,N-diethylaniline, sodium hydride, potassium hydroxide). If desired, a phase transfer catalyst (e.g. tetra-n-butylammonium bromide) can be used so as to obtain the dipropargyloxy-nitrobenzene compound (I) in a high yield. The reaction may be accomplished at a temperature of 0 to 150° C. within 10 hours.

The starting dihydroxy-nitrobenzene compound (II) is obtainable by a known method [J.Chem.Soc., 2619 (1955); Medd.Norsk.Farm. Selskap., 23, 1 (1961); J. Org. Chem., 46, 3846 (1981)].

A representative preparation procedure for the dihydroxynitrobenzene compounds (I) is illustratively shown in the following example.

EXAMPLE 1

Sodium hydride (18.4 g; 60% dispersion in mineral oil) was added to dimethylformamide (1000 ml). To the mixture was added a solution of 3-chloro-5-nitrocatechol (87.3 g) in dimethylformamide (300 ml) at a temperature of 0 to 5° C., followed by stirring at room temperature for 1 hour. Propargyl bromide (55.0 g) was added thereto. The resultant mixture was heated at 90° C. for 5 minutes and cooled to 0° C. Sodium hydride (18.4 g) was added thereto, and after foaming ceased, propargyl bromide (55.0 g) was further added. The resulting mixture was heated at 90° C. for 5 minutes, poured into ice-water and extracted with ethyl acetate. The extract was washed with aqueous potassium carbonate solution and water, dried over magnesium sulfate and concentrated under reduced pressure. The residue was purified by silica gel chromatography using toluene as the eluent to give 3-chloro-4,5-dipropargyloxy-nitrobenzene (78.5 g). m.p., 80°–83° C.

In the same manner as above, the dipropargyloxynitrobenzene compounds (I) as shown in Table 1 can be obtained.

TABLE 1

(I)

| Compound No. | X | Physical constant |
|---|---|---|
| 1 | CH₃ | NMR $\delta^{TMS}_{CDCl_3}$: 7.76 (s, 2H), 4.78–4.88 (4H), 2.45–2.56 (2H), 2.38 (s, 3H) |
| 2 | OCH₃ | m.p., 93.5–94.5° C. |
| 3 | F | NMR $\delta^{TMS}_{CDCl_3}$: 7.60–7.90 (m, 2H), 4.80–5.10 (4H), 2.50–2.70 (m, 2H) |
| 4 | Cl | m.p., 80–83° C. |
| 5 | Br | m.p., 80.5–81° C. |

In the practical usage of the dipropargyloxynitrobenzene compounds (I) as fungicides, they may be applied as such or in a formulation form such as dusts, wettable powders, oil sprays, emulsifiable concentrates, tablets, granules, fine granules, aerosols or flowables. The preparation forms can be formulated in a conventional manner by mixing at least one of the dipropargyloxynitrobenzene compounds (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents include botanical materials (e.g. flour, tobacco stalk powder, soybean powder, walnut shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, various fatty acids and their esters, etc.

The foregoing formulations generally contain at least one of the dipropargyloxy-nitrobenzene compounds (I) in a concentration of about 1 to 95% by weight, preferably of 2.0 to 80% by weight. By using the formulations, the dipropargyloxy-nitrobenzene compounds (I) are generally applied in such amounts as 2 to 100 g per 10 are.

When only the drug-resistant strains of phytopathogenic fungi are present, the dipropargyloxynitrobenzene compounds (I) may be used alone. However, when the drug-sensitive strains are present together with the drug-resistant strains, their alternate use with benzimidazole, thiophanate and/or cyclic imide fungicides or their combined use with benzimidazole, thiophanate and/or cyclic imide fungicides is favorable. In such alternate or combined use, each active ingredient may be employed as such or in conventional agricultural formulation forms. In the case of the combined use, the weight proportion of the compound (I) and the benzimidazole, thiophanate and/or cyclic imide fungicide may be from about 1:0.1 to 1:10.0.

Typical examples of the benzimidazole, thiophanate and cyclic imide fungicides which are commercially available are shown in Table 2.

TABLE 2

| Compound | Structure | Name |
|---|---|---|
| A | 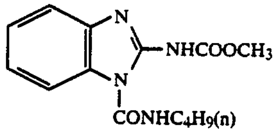 | Methyl 1-(butylcarbamoyl)benzimidazol-2-yl-carbamate |
| B | 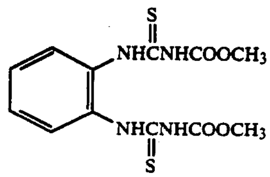 | 1,2-Bis(3-methoxycarbonyl-2-thioureido)benzene |
| C | 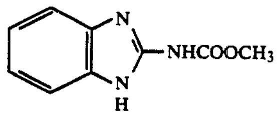 | Methyl benzimidazol-2-ylcarbamate |
| D | 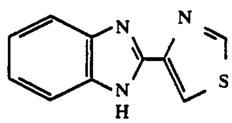 | 2-(4-Thiazolyl)benzimidazole |
| E | 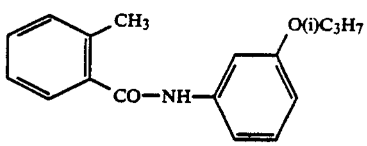 | 3'-Isopropoxy-2-methylbenzanilide |
| F | 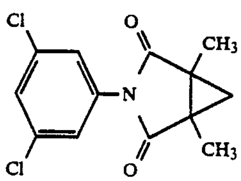 | N—(3',5'-Dichlorophenyl)-1,2-dimethylcyclopropane-1,2-dicarboximide |
| G | 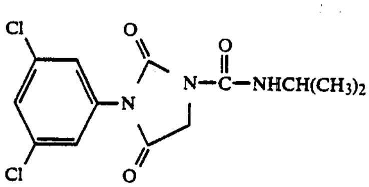 | 3-(3',5'-Dichlorophenyl)-1-isopropylcarbamoylimidazolidin-2,4-dione |
| H | 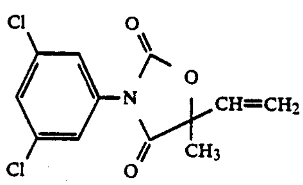 | 3-(3',5'-Dichlorophenyl)-5-methyl-5-vinyloxazolidin-2,4-dione |
| I | 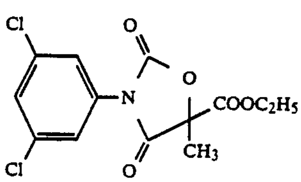 | Ethyl (RS)—3-(3',5'-dichlorophenyl)-5-methyl-2,4-dioxo-oxazolidine-5-carboxylate |

The dipropargyloxy-nitrobenzene compounds (I) may be also used in admixture with other fungicides, herbicides, insecticides, miticides, fertilizers, etc. When the dipropargyloxy-nitrobenzene compounds (I) are used as fungicides, they may be applied in such amounts as 2 to 100 grams per 10 are. However, this amount may vary depending upon the formulation forms, application times, application methods, application sites, diseases, crops and so on, and therefore, they are not limited to particular amounts.

Some practical embodiments of the fungicidal composition according to the present invention are illustratively shown in the following Examples wherein % and part(s) are by weight.

FORMULATION EXAMPLE 1

Two parts of Compound No. 1, 88 parts of kaolin clay and 10 parts of talc are thoroughly pulverized and mixed together to obtain a dust formulation containing 2% of the active ingredient.

FORMULATION EXAMPLE 2

Ten parts of Compound No. 4, 1 part of polyoxyethylene styrylphenyl ether as an emulsifier and 89 parts of water are mixed together to obtain an emulsifiable concentrate formulation containing 10% of the active ingredient.

FORMULATION EXAMPLE 3

Eighty parts of Compound No. 4, 10 parts of cyclohexanone and 10 parts of polyoxyethylene alkylaryl ether as an emulsifier are mixed together to obtain an emulsifiable concentrate formulation containing 80% of the active ingredient.

FORMULATION EXAMPLE 4

Two parts of Compound No. 1, 88 parts of clay and 10 parts of talc are thoroughly pulverized and mixed together to obtain a dust formulation containing 2% of the active ingredient.

FORMULATION EXAMPLE 5

One part of Compound No. 5, 1 part of Compound A, 88 parts of clay and 10 parts of talc are thoroughly pulverized and mixed together to obtain a dust formulation containing 2 parts of the active ingredient.

FORMULATION EXAMPLE 6

Twenty parts of Compound No. 1, 10 parts of Compound F, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder composition containing 30% of the active ingredient.

FORMULATION EXAMPLE 7

Ten parts of Compound No. 1, 40 parts of Compound B, 45 parts of diatomaceous earth, 2.5 parts of calcium alkylbenzenesulfonate as a wetting agent and 2.5 parts of calcium ligninsulfonate as a dispersing agent are mixed while being powdered to obtain a wettable powder composition containing 50% of the active ingredient.

FORMULATION EXAMPLE 8

Five parts of Compound No. 2, 5 parts of Compound C, 80 parts of cyclohexanone and 10 parts of polyoxyethylene alkylaryl ether as an emulsifier are mixed together to obtain an emulsifiable concentrate formulation containing 10% of the active ingredient.

Typical test data indicating the excellent fungicidal activity of the dipropargyloxy-nitrobenzene compounds (I) are shown below.

EXPERIMENT 1

Protective activity test on powdery mildew of cucumber (*Sphaerotheca fuliginea*):

A flower pot of 90 ml volume was filed with sandy soil, and seeds of cucumber (var: Sagami-hanjiro) were sowed therein. Cultivation was carried out in a greenhouse for 8 days. Onto the resulting seedlings having cotyledons, the test compound formulated in an emulsifiable concentrate or wettable powder and diluted with water was sprayed at a rate of 10 ml per pot. Then, the seedlings were inoculated with a spore suspension of the drug-resistant or drug-sensitive strain of *Sphaerotheca fuliginea* by spraying and further cultivated in the greenhouse. Ten days thereafter, the infectious state of the plants was observed. The degree of damage was determined in the following manner, and the results are shown in Table 3.

The leaves examined were measured for a percentage of infected area and classified into the corresponding disease indices, 0, 0.5, 1, 2, 4:

| Disease index | Percentage of infected area |
| --- | --- |
| 0 | No infection |
| 0.5 | Infected area of less than 5% |
| 1 | Infected area of less than 20% |
| 2 | Infected area of less than 50% |
| 4 | Infected area of not less than 50% |

The disease severity was calculated according to the following equation:

$$\text{Disease severity (\%)} = \frac{\Sigma\{(\text{Disease index}) \times (\text{Number of leaves})\}}{4 \times (\text{Total number of leaves examined})} \times 100$$

The prevention value was calculated according to the following equation:

$$\text{Prevention value (\%)} = 100 - \frac{(\text{Disease severity in treated plot})}{(\text{Disease severity in untreated plot})} \times 100$$

TABLE 3

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 500 | 100 | 0 |
| A | 500 | 0 | 100 |
| B | 500 | 0 | 100 |
| C | 500 | 0 | 100 |

As understood from the results shown in Table 3, the dipropargyloxy-nitrobenzene compounds (I) of the invention exhibit an excellent preventive effect on the drug-resistant strain but do not show any preventive effect on the tested drug-sensitive strain. To the contrary, benzimidazole and thiophanate fungicides such as Compounds A, B and C show a notable controlling effect on the drug-sensitive strain but not on the drug-resistant strain.

EXPERIMENT 2

Preventive effect on cercospora leaf spot of sugarbeet (*Cercospora beticola*):

A flower pot of 90 ml volume was filled with sandy soil, and seeds of sugarbeet (var: Detroit dark red) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of Cercospora beticola by spraying. The pot was covered with a polyvinyl chloride sheet to make a condition of high humidity, and cultivation was continued in the greenhouse for 10 days. The degree of damage was determined in the same manner as in Experiment 1, and the results are shown in Table 4.

TABLE 4

| Compound No. | Concentration of active ingredient (ppm) | Prevention value when inoculated with drug-resistant strain (%) | Prevention value when inoculated with drug-sensitive strain (%) |
|---|---|---|---|
| 4 | 500 | 100 | 0 |
| A | 500 | 0 | 100 |
| B | 500 | 0 | 100 |
| C | 500 | 0 | 100 |

As understood from the results shown in Table 4, the dipropargyloxy-nitrobenzene compounds (I) of the invention show an excellent preventive effect on the drug-resistant strain but do not show any preventive effect on the tested drug-sensitive strain. To the contrary, benzimidazole and thiophanate fungicides such as Compounds A, B and C demonstrate a notable controlling effect on the drug-sensitive strain but not on the drug-resistant strain.

EXPERIMENT 3

Preventive effect on scab of pear (Venturia nashicola):

A plastic pot of 90 ml volume was filled with sandy soil, and seeds of pear (var: Chojuro) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of Venturia nashicola by spraying. The resulting plants were placed at 20° C. under a condition of high humidity for 3 days and then at 20° C. under irradiation with a fluorescent lamp for 20 days. The degree of damage was determined in the same manner as in Experiment 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
|---|---|---|---|
| 4 | 500 | 100 | 0 |
| A | 500 | 0 | 100 |
| B | 500 | 0 | 100 |

As understood from the results shown in Table 5, the dipropargyl-nitrobenzene compounds (I) of the invention demonstrate an excellent preventive effect on the drug-resistant strain but do not show any preventive effect on the tested drug-sensitive strain. To the contrary, benzimidazole and thiophanate fungicides such as Compounds A and B show a notable controlling effect on the drug-sensitive strain but not on the drug-resistant strain.

EXPERIMENT 4

Preventive effect on brown leaf-spot of peanut (Cercospora arachidicola):

Plastic pots of 90 ml volume were filled with sandy soil, and seeds of peanut (var: Chiba hanryusei) were sowed therein. Cultivation was carried out in a greenhouse for 14 days. Onto the resulting seedlings, the test compound formulated in an emulsifiable concentrate or wettable powder and diluted with water was sprayed at a rate of 10 ml per pot. Then, the seedlings were inoculated with a spore suspension of the drug-sensitive strain of Cercospora arachidicola by spraying. The resulting plants were covered with a polyvinyl chloride sheet to make a condition of humidity and cultivated in the geeenhouse for 10 days. The degree of damage was determined in the same manner as in Experiment 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
|---|---|---|---|
| 5 | 500 | 100 | 0 |
| A | 500 | 0 | 100 |
| B | 500 | 0 | 100 |

As understood from the results shown in Table 6, the dipropargyloxy-nitrobenzene compounds (I) of the invention show an excellent preventive effect on the drug-resistant strain but do not show any preventive effect on the tested drug-sensitive strain. To the contrary, benzimidazole and thiophanate fungicides such as Compounds A and B show a notable controlling effect on the drug-sensitive strain but not on the drug-resistant strain.

EXPERIMENT 5

Preventive effect on gray mold of cucumber (Botrytis cinerea):

Plastic pots of 90 ml volume were filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in an emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of Botrytis cinerea by putting them on the leaf surfaces. After the plants were infected by incubating under high humidity at 20° C. for 3 days, the rates of disease severity were observed. The degree of damage was determined in the same manner as in Experiment 1, and the results are shown in Table 7.

TABLE 7

| Compound No. | Concentration of active ingredient (ppm) | Prevention value when inoculated with drug-resistant strain (%) | Prevention value when inoculated with drug-sensitive strain (%) |
|---|---|---|---|
| 1 | 200 | 88 | 0 |
|   | 50 | 88 | 0 |
|   | 12.5 | 84 | 0 |
| 2 | 200 | 94 | 0 |
|   | 50 | 88 | 0 |

TABLE 7-continued

| Compound No. | Concentration of active ingredient (ppm) | Prevention value when inoculated with drug-resistant strain (%) | Prevention value when inoculated with drug-sensitive strain (%) |
|---|---|---|---|
|  | 12.5 | 56 | 0 |
| 3 | 200 | 100 | 0 |
|  | 50 | 100 | 0 |
|  | 12.5 | 94 | 0 |
| 4 | 200 | 100 | 0 |
|  | 50 | 100 | 0 |
|  | 12.5 | 91 | 0 |
| 5 | 200 | 100 | 0 |
|  | 50 | 94 | 0 |
|  | 12.5 | 88 | 0 |
| A | 200 | 0 | 100 |
| B | 200 | 0 | 100 |

As understood from the results shown in Table 7, the dipropargyloxy-nitrobenzene compounds (I) of the invention show an excellent preventive effect on the drug-resistant strain but do not show any preventive effect on the tested drug-sensitive strain. To the contrary, benzimidazole and thiophanate fungicides such as Compounds A and B show a notable controlling effect on the drug-sensitive strain but not on the drug-resistant strain.

EXPERIMENT 6

Preventive effect on gummy stem blight of cucumber (*Mycosphaerella melonis*):

Plastic pots of 90 ml volume were filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Mycosphaerella melonis* by putting them on the leaf surfaces. After the plants were infected by incubating under high humidity at 25° C. for 4 days, the rates of disease severity were observed. The degree of damage was determined in the same manner as in Experiment 1, and the results are shown in Table 8.

TABLE 8

| Compound No. | Concentration of active ingredient (ppm) | Prevention value when inoculated with drug-resistant strain (%) | Prevention value when inoculated with drug-resistant strain (%) |
|---|---|---|---|
| 4 | 500 | 100 | 0 |
| A | 500 | 0 | 100 |
| B | 500 | 0 | 100 |

As understood from the results shown in Table 8, the dipropargyloxy-nitrobenzene compounds (I) of the present invention show an excellent preventive effect on the drug-resistant strain but do not show any preventive effect on the tested drug-sensitive strain. To the contrary, benzimidazole and thiophanate fungicides such as Compuonds A and B show a notable controlling effect on the drug-sensitive strain but not on the drug-resistant strain.

EXPERIMENT 7

Preventive effect on sheath blight of rice (*Rhizoctonia solani*):

Sandy loam was filled in a plastic pot and rice (var.: Kinki No. 33) was sowed and cultivated in a greenhouse for 28 days to grow to seedlings. The test compounds were formulated into emulsifiable concentrates in accordance with the Formulation Example 3 and diluted with water to a given concentration. These were foliar-sprayed onto the seedlings to allow them to deposit thoroughly on the leaf surface. After 4 hours from the spraying, the seedlings were inoculated by putting agar piece containing *Rhizoctonia solani*. After inoculation, the seedlings were grown at 28° C. for 4 days under highly humid condition and the controlling effects were observed. The results are shown in Table 9.

The controlling effect is determined by observing with the naked eye the condition of disease of test plants, namely, the degree of fungus colony and infected area of leaf and stem and grading the condition of diseases into the following six steps 0, 1, 2, 3, 4 and 5:

5 No infected area and fungus colony are noticed.
4 Infected area and fungus colony are noticed in about 10% of leaf and stem.
3 Infected area and fungus colony are noticed in about 30% of leaf and stem.
2 Infected area and fungus colony are noticed in about 50% of leaf and stem.
1 Infected area and fungus colony are noticed in about 70% of leaf and stem.
0 Infected area and fungus colony are noticed in more than about 70% and no difference is noticed from the condition of disease when no compound is used.

TABLE 9

| Compound No. | Concentration of active ingredient (ppm) | Controlling effect |
|---|---|---|
| 4 | 500 | 5 |
| E | 500 | 5 |

EXPERIMENT 8

Preventive effect on powdery mildew of cucumber (*Sphaerotheca fuliginea*):

A plastic pot of 90 ml volume was filled with sandy soil, and seeds of cucumber (var: Sagami-hanjiro) were sowed therein. Cultivation was carried out in a greenhouse for 8 days. Onto the resulting seedlings having cotyledons, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Sphaerotheca fuliginea* by spraying and further cultivated in the greenhouse. Ten days thereafter, the infectious state of the plants was observed. The degree of damage was determined in the same manner as in Experiment 1, and the results are shown in Table 10.

TABLE 10

| Compound No. | Concentration of active ingredient (ppm) | Prevention value (%) |
|---|---|---|
| 2 | 100 | 36 |
| 2 | 20 | 0 |
| 3 | 100 | 40 |
| 3 | 20 | 0 |
| 4 | 100 | 46 |
| 4 | 20 | 0 |

TABLE 10-continued

| Compound No. | Concentration of active ingredient (ppm) | Prevention value (%) |
|---|---|---|
| A | 100 | 45 |
| A | 20 | 12 |
| B | 100 | 44 |
| B | 20 | 10 |
| C | 100 | 42 |
| C | 20 | 8 |
| D | 500 | 42 |
| D | 100 | 10 |
| 2 + A | 20 + 20 | 100 |
| 2 + B | 20 + 20 | 100 |
| 3 + A | 20 + 20 | 100 |
| 3 + B | 20 + 20 | 100 |
| 3 + C | 20 + 20 | 100 |
| 3 + D | 20 + 20 | 100 |
| 4 + A | 20 + 20 | 100 |
| 4 + B | 20 + 20 | 100 |
| 4 + C | 20 + 20 | 100 |

As understood from the results shown in Table 10, the combined use of the dipropargyloxy-nitrobenzene compounds (I) of the present invention with benzimidazole, thiophanate and/or cyclic imide fungicides show a much greater preventive effect than their sole use.

EXPERIMENT 9

Preventive effect on gray mold of tomato (*Botrytis cinerea*):

A plastic pot of 90 ml volume was filled with sandy soil, and seeds of tomato (var: Fukuju No. 2) were sowed therein. Cultivation was carried out in a greenhouse for 4 weeks. Onto the resulting seedlings at the 4-leaf stage, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damage was determined in the same manner as in Experiment 1, and the results are shown in Table 11.

TABLE 11

| Compound No. | Concentration of active ingredient (ppm) | Prevention value (%) |
|---|---|---|
| 2 | 100 | 32 |
| 2 | 20 | 0 |
| 3 | 100 | 34 |
| 3 | 20 | 0 |
| 4 | 100 | 30 |
| 4 | 20 | 0 |
| F | 100 | 48 |
| F | 20 | 22 |
| G | 500 | 46 |
| G | 100 | 18 |
| H | 100 | 42 |
| H | 20 | 15 |
| I | 500 | 42 |
| I | 100 | 12 |
| 2 + F | 20 + 50 | 100 |
| 2 + G | 20 + 50 | 100 |
| 2 + H | 20 + 50 | 100 |
| 2 + I | 20 + 50 | 100 |
| 3 + I | 20 + 50 | 100 |
| 3 + H | 20 + 50 | 100 |
| 4 + F | 20 + 50 | 100 |
| 4 + I | 20 + 50 | 100 |

As understood from the results shown in table 11, the combined use of the dipropargyloxy-nitrobenzene compounds (I) of the present invention with benzimidazole, thiophanate and/or cyclic imide fungicides show a much greater preventive effect than their sole use.

The inventive being thus described, it will be obvious that the same may be varied in many ways. Such variations are not to be reguarded as a departure from the spirit and scope of the invention, and all such modifications as would be obvious to one skilled in the art are intended to be included within the scope of the following claims.

What is claimed is:

1. A fungicidal composition which comprises as an active ingredient a fungicidally effective amount of at least one compound of the formula:

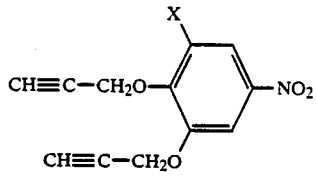

wherein X is a halogen atom, a $C_1$–$C_3$ alkyl group or a $C_1$–$C_3$ alkoxy group, and an inert carrier or diluent.

2. The fungicidal composition according to claim 1, which further comprises as an additional active ingredient(s) a member selected from the group consisting of a benzimidazole, thiophanate and cyclic imide fungicide in an amount of 1:0.1 to 1:10.0 parts by weight with respect to the compound to said additional active ingredient.

3. The fungicidal composition according to claim 2, wherein the additional active ingredient is methyl 1-(butylcarbamoyl)benzimidazol-2-yl-carbamate, 2-(2-furyl)benzimidazol, 2-(4-thiazolyl)benzimidazole, methyl benzimidazol-2-ylcarbamate, 1,2-bis(3-methoxycarbonyl-2-thioureido)benzene, 1,2-bis(3-ethoxycarbonyl-2-thioureido)benzene, 2-(O,S-dimethylphosphorylamino)-1-(3'-methoxycarbonyl-2'-thioureido)-benzene, 2-(O,O-dimethylthiophosphorylamino)-1-(3'-methoxycarbonyl-2'-thioureido)benzene, 3-(3',5'-dichlorophenyl)-1,2-dimethylcyclopropane-1,2-dicarboximide, 3-(3',5'-dichlorophenyl)-1-isopropylcarbamoylimidazolidine- 2,4-dione, 3-(3',5'-dichlorophenyl)-5-methyl-5-vinyloxazoline-2,4-dione or ethyl (RS)-3-(3',5'-dichlorophenyl)-5-methyl-2,4-dioxooxazolidine-5-carboxylate.

4. The fungicidal composition according to claim 1, which is effective for plant pathogenic fungi having a drug-resistance.

5. The composition according to claim 1, wherein X is methyl.

6. The composition according to claim 1, wherein X is methoxy.

7. The composition according to claim 1, wherein X is fluorine.

8. The composition according to claim 1, wherein X is chlorine.

9. The composition according to claim 1, wherein X is bromine.

10. A method for controlling plant pathogenic fungi which comprises applying a fungicidally effective amount of at least one compound of the formula:

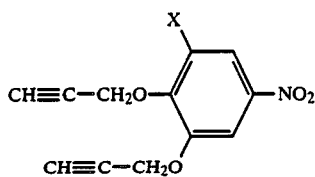

wherein X is a halogen atom, a $C_1$-$C_3$ alkyl group or a $C_1$-$C_3$ alkoxy group to plant pathogenic fungi.

11. The method according to claim 4, wherein the plant pathogenic fungi is a drug-resistant strain.

12. A method for controlling plant pathogenic fungi which comprises applying a fungicidally effective amount of a mixture of the (a) compound of the formula:

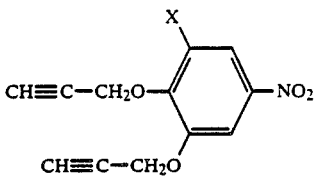

wherein X is a halogen atom, a $C_1$-$C_3$ alkyl group or a $C_1$-$C_3$ alkoxy group and (b) a benzimidazole, thiophanate or cyclic imide fungicide to plant pathogenic fungi in an amount of 1:0.1 to 1:10.0 parts by weight with respect to said (a):(b).

13. The method according to claim 10, wherein X is methyl.

14. The method according to claim 10, wherein X is methoxy.

15. The method according to claim 10, wherein X is fluorine.

16. The method according to claim 10, wherein X is chlorine.

17. The method according to claim 5, wherein X is bromine.